(12) United States Patent
Levy (10) Patent No.: US 10,149,816 B2
(45) Date of Patent: Dec. 11, 2018

(54) **SKIN COSMETIC COMPOSITIONS COMPRISING *MALUS DOMESTICA* EXTRACT AND *ARGANIA SPINOSA* SPROUT EXTRACT FOR IMPROVING SKIN APPEARANCE**

(76) Inventor: Phillip Levy, Geneva (CH)

( * ) Notice: Subject to any disclaimer, the term of this patent is extended or adjusted under 35 U.S.C. 154(b) by 1209 days.

(21) Appl. No.: 14/126,132

(22) PCT Filed: Jun. 13, 2012

(86) PCT No.: PCT/CA2012/000584
§ 371 (c)(1),
(2), (4) Date: Mar. 26, 2014

(87) PCT Pub. No.: WO2012/171106
PCT Pub. Date: Dec. 20, 2012

(65) Prior Publication Data
US 2015/0147360 A1    May 28, 2015

Related U.S. Application Data

(60) Provisional application No. 61/496,386, filed on Jun. 13, 2011.

(51) Int. Cl.
| | |
|---|---|
| *A61K 36/00* | (2006.01) |
| *A61K 36/73* | (2006.01) |
| *A61K 36/53* | (2006.01) |
| *A61K 36/886* | (2006.01) |
| *A61K 8/97* | (2017.01) |
| *A61Q 19/08* | (2006.01) |
| *A61K 8/11* | (2006.01) |
| *A61K 8/60* | (2006.01) |
| *A61K 8/64* | (2006.01) |
| *A61K 8/67* | (2006.01) |
| *A61K 8/73* | (2006.01) |
| *A61K 8/92* | (2006.01) |
| *A61Q 19/00* | (2006.01) |

(52) U.S. Cl.
CPC .............. *A61K 8/97* (2013.01); *A61K 8/11* (2013.01); *A61K 8/602* (2013.01); *A61K 8/64* (2013.01); *A61K 8/67* (2013.01); *A61K 8/735* (2013.01); *A61K 8/738* (2013.01); *A61K 8/92* (2013.01); *A61Q 19/00* (2013.01); *A61Q 19/08* (2013.01); *A61K 2800/88* (2013.01)

(58) Field of Classification Search
CPC .............................. A61K 36/73; A61K 36/185
USPC ................................ 424/765, 774, 776, 777
See application file for complete search history.

(56) References Cited

U.S. PATENT DOCUMENTS

| | | | |
|---|---|---|---|
| 2007/0196293 A1* | 8/2007 | Zhang | A61K 9/7015 424/59 |
| 2007/0281047 A1* | 12/2007 | Henry | A61K 8/97 424/776 |
| 2008/0299092 A1* | 12/2008 | Blum | A61K 8/14 424/93.7 |

FOREIGN PATENT DOCUMENTS

| | | | | |
|---|---|---|---|---|
| CN | 101467945 A | * | 7/2009 | ............ A61K 8/97 |
| DE | 102007062113 A1 | * | 6/2009 | ............ A61K 8/044 |
| EP | 2082730 A2 | * | 7/2009 | ............ A61K 8/965 |
| JP | 2013-147479 | | 8/2013 | |
| WO | WO 2010/067212 A2 | | 6/2010 | |
| WO | WO 2012/018643 | | 2/2012 | |

OTHER PUBLICATIONS

Fuchs et al. "Encapsulation of oil in powder using spray drying and fluidised bed agglomeration", Journal of Food Engineering, Jul. 2006, pp. 27-35.*
"Anti-Wrinkle Eye Cream," Database GNPD, Mintel, XP002735905, Jan. 2010, 4 pages.
"Creme Advanced," Database GNPD, Mintel, XP 002735903, Feb. 2011, 6 pages.
"Moisturising Repair Balm," Database GNPD, Mintel, XP002735902, Oct. 2010, 4 pages.
"PhytoCellTech™ *Malus domestica,*" Mibellebiochemistry, May 5, 2008, XP 002735907, 38 pages.
"Skin Repair Serum," Database GNPD, Mintel, XP 002735904, Sep. 2010, 8 pages.
"Vitalizing Dermal Stem Cells—Our Next Target / PhytoCellTech™ Argan," Mibellebiochemistry, XP 002735906, Apr. 1, 2011, 20 pages.
Extended European Search Report for European Patent Application No. 12799831.8, dated Mar. 31, 2015, 9 pages.
International Search Report prepared by the Canadian Intellectual Property Office dated Sep. 11, 2012, for International Application No. PCT/CA2012/000584.
SpecialChem website, "Mibelle Biochemistry Introduces PhytoCellTec™ Argan having Significant Anti-aging Properties", Apr. 4, 2011 (Apr. 4, 2011) http://www.specialchem4cosmetics.com/services/news.aspx?id=6416.
Schmid, D. and Zulli, F., "Stimulating Epidermal Regeneration with Plant-derived Stem Cells", Cosmeto-Scientifique—SCC Chapitre du Quebec, Aug. 2010, vol. 11, No. 3, p. 4-9.
Schmid, D. et al., "Plant Stem Cell Extract for Longevity of Skin and Hair", SOFW-Journal, 2008, vol. 134, No. 5, p. 30-35.
Schmid, D. et al., "Stimulation of stem cells for real rejuvenation", Mibelle Biochemistry, Aug. 2008. http://www.mibellebiochemistry.com/pdfs/Stimulation_of_stem_cells_for_real_skin_rejuvenation_CosmeticsDesign_08_2008.pdf.

(Continued)

*Primary Examiner* — Christopher R Tate
*Assistant Examiner* — Deborah A Davis
(74) *Attorney, Agent, or Firm* — Sheridan Ross P.C.

(57) ABSTRACT

A formulation and/or composition comprising an epidermal stem cells activator and a dermal stem cells activator that have the potential of improving skin appearance. Methods of using such formulation and/or composition to improve skin appearance and to activate constituents of the skin.

9 Claims, 2 Drawing Sheets

(56) References Cited

OTHER PUBLICATIONS

Isomers Website, Isomers® Skincare Newsletter, announcement of the launching of "Relysage® Wrinkle Liberator" product. http://www.isomers.ca/NewsLetter.aspx?BulletinID=94 Ingredients in Relysage® Wrinkle Liberator: http://www.isomers.ca/Product.aspx?Tab=Formulation&ProductID=716.

Website Bernama Media Relations and Event Management; "Gocell International Launches Rejuvenist™; A Phenomenal Cell Perfection Super Serum for Anti-Aging", Jul. 8, 2011. http://mrem.bernama.com/viewsm.php?idm=17737 Ingredients in Rejuvenist™: http://www.nature12u.com/rejuvenist.html.

LeShop.ch Website, Zoe Effect Night Renewal Booster with PhytoCell Tec http://www.leshop.ch/leshop/Main.do/direct/fr/Supermarche/_/_/328031_Zoe_Night_Booster_30ml#/fr/Supermarche/_/_/328031_Zoe_Night_Booster_30ml.

\* cited by examiner

SKIN COSMETIC COMPOSITIONS COMPRISING *MALUS DOMESTICA* EXTRACT AND *ARGANIA SPINOSA* SPROUT EXTRACT FOR IMPROVING SKIN APPEARANCE

CROSS REFERENCE TO RELATED APPLICATION

This application is a national stage application under 35 U.S.C. 371 of PCT Application No. PCT/CA2012/000584 having an international filing date of 13 Jun. 2012, which designated the United States, which PCT application claimed the benefit of U.S. Application Ser. No. 61/496,386, filed 13 Jun. 2011, the contents of each of which are incorporated herein by reference in their entirety.

FIELD OF TECHNOLOGY

The present invention relates to formulations, compositions and methods for cosmetic skin care.

BACKGROUND INFORMATION

Main skin treatments used today are related to skin treatment that have active principles, natural or synthetic, which mainly act on the superficial layer of the skin in order to, for example, prevent or limit the effects of skin ageing or to treat skin damage.

Generally, a skin recovery cosmetic functionally acts on the hydration of superficial layers of the skin, reducing as far as possible the loss of water in the cells and thus restoring the turgidity of the skin.

One of the limits of today's cosmetic treatments is the fact that such treatments substantially involve the superficial layer of the skin, and do not address or eliminate the causes of skin ageing and/or the causes of skin damage. Consequently, these treatments have to be repeated over time and they are not suitable for providing stable results.

There is thus a need in the art for formulations and/or compositions and methods that provide superior and stable prevention, treatment and/or repair of the skin.

SUMMARY

According to one aspect, the present invention provides a cosmetic composition for application on skin of a subject, comprising an epidermis activator and a dermis activator.

According to another aspect, the present invention provides a cosmetic composition for application on skin of a subject, comprising between about 0.01% and about 10% by weight of the composition of *malus domestica* extract; and between about 0.01% and about 5% by weight of the composition of *argania spinosa* sprout extract; wherein the *argania spinosa* sprout extract is encapsulated.

According to another aspect, the present invention provides a method for improving overall skin appearance through activation of skin stem cells, comprising applying to the skin the cosmetic composition as defined herein.

According to another aspect, the present invention provides a method for delaying onset of skin ageing through activation of skin stem cells, comprising applying to the skin the cosmetic composition as defined herein.

According to another aspect, the present invention provides a method for improving overall appearance of skin through activation of skin stem cells, comprising the steps of applying to the skin the composition as defined herein; and applying to the skin the composition as defined herein.

According to another aspect, the present invention provides a method for delaying onset of skin ageing through activation of skin stem cells, comprising the steps of applying to the skin the composition as defined herein; and applying to the skin the composition as defined herein.

According to another aspect, the present invention provides a kit for improving overall appearance of skin through activation of skin stem cells, comprising the cosmetic composition as defined herein, together with instructions for improving the overall appearance of skin.

According to another aspect, the present invention provides a kit for delaying onset of skin ageing through activation of skin stem cells, comprising the cosmetic composition as defined herein, together with instructions for delaying onset of skin ageing.

According to another aspect, the present invention provides a kit assembly for improving overall appearance of skin through activation of skin stem cells, comprising a first container comprising a cosmetic serum, the cosmetic serum comprising between about 0.01% and about 10% by weight of the cosmetic serum of *malus domestica* extract and between about 0.01% and about 5% by weight of the cosmetic serum of *argania spinosa* sprout extract; and a second container comprising a cream, the cream comprising between about 0.01% and about 10% by weight of the cream of *malus domestica* extract and between about 0.01% and about 5% by weight of the cream of *argania spinosa* sprout extract; wherein the first container is provided with instructions for application of the cosmetic serum onto skin and the second container is provided with instructions for application of the cream onto skin.

DETAILED DESCRIPTION

The inventors of the present invention have conceived a cosmetic skin treatment that provides superior rejuvenation and revitalization of the overall look of the skin. More specifically, the inventors have created formulations and/or compositions for application to the skin that have the potential of promoting activation, vitalization and regeneration of the epidermis, in particular of the epidermal stem cells and that have the potential to also promote activation and regeneration of the dermis, in particular, the dermal stem cells.

According to one embodiment of the present invention, the formulations and/or compositions defined herein comprise one or more skin stem cells activator agent. In one implementation of this embodiment, the one or more skin stem cells activator agent is an epidermal stem cells activator (or an epidermal stem cells potentiator). According to another implementation, the one or more skin stem cells activator agent is a dermal stem cells activator (or a dermal stem cells potentiator). According to yet another implementation, the one ore more skin stem cells activator agent is a combination of an epidermal stem cells activator and a dermal stem cells activator.

Are thus defined herein, cosmetic formulations and/or compositions that comprise an epidermis activator, more particularly an epidermal stem cells activator; and cosmetic formulations and/or compositions that comprise a dermis activator, more particularly a dermal stem cells activator.

Are also defined herein, cosmetic formulations and/or compositions that comprise an epidermis as well as a dermis activator, more particularly that comprise an epidermal stem cells activator and a dermal stem cells activator. A combination of epidermal with dermal stem cell activators has the potential to enhance youthfulness of the skin resulting in superior (compared to the use of either epidermal or dermal stem cells activators individually) firming, skin thickness, collagen production and overall quality of skin anti-ageing characteristics.

Are also defined herein, cosmetic formulations and/or compositions that comprise an epidermis vitalization agent, more particularly an epidermal stem cells vitalization agent; cosmetic formulations and/or compositions that comprise a dermis vitalization agent, more particularly a dermal stem cells vitalization agent; and cosmetic formulations and/or compositions that comprise epidermis and dermis vitalization agent, more particularly an epidermal stem cells vitalization agent as well as a dermal stem cells vitalization agent.

The expressions "epidermal stem cells activator" and "epidermal stem cells potentiator", as used interchangeably herein, unless otherwise specified, refer to an agent that promotes growth, vitalization, regeneration and/or survival of epidermal stem cells and/or that promotes or maintains a healthy epidermis and/or epidermal stem cells. As used herein, the expression "healthy epidermal stem cells" refers to epidermal stem cells that perform the biological and biochemical activities and functions of wild type epidermal stem cells.

The expressions "dermal stem cells activator" and "dermal stem cells potentiator", as used interchangeably herein, unless otherwise specified, refer to an agent that promotes growth, vitalization, regeneration and/or survival of dermal stem cells and/or that promotes or maintains a healthy dermis and/or dermal stem cells. As used herein, the expression "healthy dermal stem cells" refers to dermal stem cells that perform the biological and biochemical activities and functions of wild type dermal stem cells.

The epidermal stem cells activator and the dermal stem cells activator may be incorporated into the formulations and/or compositions of the invention together with at least one other active ingredient that promotes or maintains healthy epidermis/dermis and/or epidermal and/or dermal stem cells.

The formulation and/or compositions defined herein have the potential to be used for protecting, enhancing and/or vitalizing skin stem cells, particularly, epidermal and/or dermal stem cells. They also have the potential to provide unexpected stimulatory effects on epidermal and/or dermal regeneration. They have the potential to enhance youthfulness of the skin, to improve firmness, thickness, collagen production and overall quality of anti-ageing characteristics of the skin as well as the potential to protect longevity of epidermal and/or dermal stem cells.

The formulations and/or compositions defined herein also have the potential to accelerate skin's natural repair process, to reduce depth of wrinkles, to reactivate the skin's youthful functions, to delay onset of senescence of epidermal stem cells, to hydrate the skin, to improve skin suppleness and elasticity and/or to improve texture of the skin.

The term "skin", as used herein unless otherwise specified, refers to an outer covering of an animal, in particular a vertebrate. Mammalian skin is composed of two primary layers, namely, the epidermis, which provides waterproofing and serves as a barrier to infection; and the dermis, which serves as a location for the appendages of the skin.

The epidermis is the outermost layer of the skin. It forms the protective wrap over the body's surface and is made up of stratified squamous epithelium with an underlying basal lamina. Cell types that make up the epidermis include Merkel cells, keratinocytes, melanocytes and Langerhans cells.

The dermis is the layer of skin beneath the epidermis that comprises connective tissue. The dermis also comprises many mechanoreceptors (nerve endings) that provide the sense of touch and heat. It comprises the hair follicles, sweat glands, sebaceous glands, apocrine glands, lymphatic vessels and blood vessels.

Recently, Biernaskie J. et al. isolated dermal stem cells and identified their location (Ref. 1).

In another implementation, the epidermal stem cells activator and/or the dermal stem cells activator include *argania spinosa*, most particularly, *argania spinosa* sprout cell extract. In yet another implementation, the dermal stem cells activator is *argania spinosa*, more particularly, *argania spinosa* sprout cell extract.

*Argania spinosa* is a plant tree found predominantly in Morocco on the west side of the Atlas mountain range. The extracts may be prepared by extraction methods, such as, but not limited to maceration, remaceration, digestion, agitation maceration, fluidized-bed extraction, ultrasound extraction, countercurrent extraction, percolation, repercolation, evacolation (extraction under reduced pressure), diacolation and solid-liquid extraction under continuous reflux which is carried out in a Soxhlet extractor, each of which is known to the person skilled in the art. Solvents which can be used for carrying out the extractions are preferably organic solvents, water or mixtures of organic solvents and water, in particular low molecular weight alcohols, esters, ethers, ketones or halogen-containing hydrocarbons with greater or lesser water contents (distilled or undistilled), preferably aqueous, alcoholic solutions with greater or lesser water contents. Particular preference is given to the extraction with water, methanol, ethanol, propanol, butanol and isomers thereof, acetone, propylene glycols, polyethylene glycols, ethyl acetate, dichloromethane, trichloromethane, and mixtures thereof. The extraction usually takes place at about 20° to about 100° C., preferably at about 80° to about 100° C., in particular at the boiling temperature of the solvents or solvent mixtures. The extraction may be carried out under an inert gas atmosphere to avoid oxidation of the ingredients of the extract. The extraction times may be adjusted by the person skilled in the art depending on the starting material, the extraction method, the extraction temperature, the ratio of solvent to raw material, etc. After the extraction, the resulting crude extracts can optionally be subjected to further customary steps, such as, for example, purification, concentration and/or decoloration. If desired, the extracts prepared in this way can, for example, be subjected to selective removal of individual undesired ingredients. The extraction can be carried out to any desired degree of extraction.

In a further implementation of this embodiment, the resulting *argania spinosa* sprout cell extract is encapsulated. Encapsulation of the *argania spinosa* sprout cell extracts allows to deliver the extract deeper into the skin. In some variants of this implementation, the encapsulation is a double encapsulation. Methods and techniques for encapsulation are known in the art.

The total amount of *argania spinosa* sprout cell extract which may be incorporated into the formulations and/or compositions of the present invention varies depending on the area of the skin to which the formulation and/or the composition is to be applied.

For example, for a formulation and/or a composition that is to be applied on the skin of the face, the amount of *argania spinosa* sprout cell extract to be present in the formulations and/or compositions may range from about 0.01% to about 5% by weight, preferably from about 0.05% to about 2% by weight, more preferably from about 0.05% to about 1%, even more preferably from about 0.05% to about 0.5% by weight of the formulation and/or the composition.

For a formulation and/or a composition that is to be applied on the skin of the contour of the eyes, the amount of *argania spinosa* sprout cell extract to be present in the formulation and/or composition may range from about 0.1% to about 5% by weight, preferably from about 0.2% to about 1% by weight, more preferably about 0.4% by weight of the formulation and/or composition.

In some other implementations, the epidermal stem cells activator and/or the dermal stem cells activator include a *malus domestica* extract. In yet other implementations, the epidermal stem cells activator is a *malus domestica* extract.

The longevity effects of *malus domestica* on epidermal stem cells have been proposed before by Schmid et al. (Ref. 2).

The *malus domestica* extract is obtainable by extraction methods and techniques that are known in the art.

The total amount of *malus domestica* extract which is present in the formulation and/or composition of the present invention varies depending on the area of the skin to which the formulation and/or the composition is to be applied.

For example, for a formulation and/or a composition that is to be applied on the skin of the face, the amount of *malus domestica* extract to be present in the formulation and/or the composition may range from about 0.01% to about 10% by weight, preferably from about 0.05% to about 5% by weight, more preferably from about 0.05% to about 2% by weight, even more preferably from about 0.05% to about 1% by weight of the formulation and/or the composition.

For a formulation and/or a composition that is to be applied on the skin of the contour of the eyes, the amount of *malus domestica* extract to be present in the formulation and/or the composition may range from about 0.01% to about 10% by weight, preferably from about 0.1% to about 5% by weight, more preferably about 2% weight of the formulation and/or the composition.

According to one implementation and in addition to *argania spinosa* sprout cell extract and *malus domestica* fruit cell culture extract, the formulations and/or the compositions of the present invention may also comprise peptides, vitamins, sodium hyaluronate, aloe juice and/or *melissa officinalis* leaf extract.

According to another implementation, the formulations and/or compositions of the present invention comprise, but are not limited to, *argania spinosa* sprout cell extract, isomalt, lecithin, *malus domestica* fruit cell culture extract, peptides, vitamins, sodium hyaluronate, aloe barbadensis leaf juice, *melissa officinalis* leaf extract, carnosine (beta-alanyl-L-histidine) and cyclodextran.

According yet another implementation, the formulations and/or compositions of the present invention comprise, but are not limited to, *argania spinosa* sprout cell extract, isomalt, lecithin, *malus domestica* fruit cell culture extract, tripeptides, vitamins, sodium hyaluronate, aloe barbadensis leaf juice, *melissa officinalis* leaf extract, carnosine, cyclodextran, squalane and *butyrospermum parkii* (shea butter).

According to yet another implementation, the formulations and/or compositions of the present invention comprise, but are not limited to, *butyrospermum parkii*, *melissa officinalis* leaf extract, *malus domestica* fruit cell culture extract, argania *spinosa* sprout cell extract, *borago officinalis* seed oil, *brassica campestris* seed oil, *rosmarinus officinalis* leaf extract, *psilanthus bengalensis* leaf cell culture extract and *elaeis guineensis* oil.

The peptides useful in the formulations and/or compositions defined herein include, but are not limited to, dipeptides, tripeptides, tetrapeptides and/or peptides comprising more than four amino acids. In one implementation, the composition comprises a tripeptide, exemplary tripeptides include, but are not limited to: eisenin (a peptide with immunological activity that is isolated from the Japanese marine alga), eisenia bicyclis, glutathione (γ-L-glutamyl-L-cysteinylglycine), isoleucine-proline-proline (IPP), leupeptin (N-acetyl-L-leucyl-L-leucyl-L-argininal), melanostatin (prolyl-leucyl-glycinamide), ophthalmic acid (L-γ-glutamyl-L-α-aminobutyryl-glycine), norophthalmic acid (y-glutamyl-alanyl-glycine), and hyrotropin-releasing hormone (TRH, thyroliberin or protirelin) (L-pyroglutamyl-L-histidinyl-L-prolinamide). For example, the tripeptide may be tetradecyl aminobutyroylvalylaminobutyric urea trifluoroacetate.

The vitamins useful in the formulations and/or compositions defined herein include, but are not limited to, vitamin A, vitamin B1, vitamin B2, vitamin B3, vitamin B4, vitamin B5, vitamin B6, vitamin B7, vitamin B8, vitamin B9, vitamin B10, vitamin B11, vitamin B12, vitamin B13, vitamin B14, vitamin B15, vitamin B16, vitamin B17, vitamin Bc, vitamin Bh, vitamin Bp, vitamin Bt, vitamin Bx, vitamin Bw, vitamin C, vitamin D, vitamin E, vitamin F, vitamin G, vitamin H, vitamin I, vitamin J, vitamin K, vitamin L1, vitamin L2, vitamin M, vitamin N, vitamin O, vitamin P, vitamin PP, vitamin Q, vitamin R, vitamin S, vitamin T and vitamin U. For example, the vitamins may be vitamin A, vitamin C, vitamin E and vitamin PP.

The skin cells activator agent of the invention can be used in combination with at least one other active ingredient in a cosmetic formulation. Such other agents may include, but are not limited to: antimicrobials, antioxidants, antiperspirants, antistatic agents, binders, biological additives, botanicals, colorants, deodorants, depilating agents, emollients, emulsifiers, emulsion stabilizers, humectants, preservatives, reducing agents, solvents, surfactants, thickeners, UV absorbers and viscosity enhancers.

Examples of emulsifiers that may be included in the formulations an/or compositions of the present invention include, but are not limited to, alkyl and/or alkenyl oligoglycosides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; block copolymers, e.g. polyethylene glycol-30 dipolyhydroxystearates; polymer emulsifiers; polyalkylene glycols, and glycerol carbonate.

Examples of surfactants that may be included in the formulations and/or compositions of the present invention include, but are not limited to, anionic, nonionic, cationic and/or amphoteric or amphoteric surfactants. Examples of anionic surfactants are soaps, alkylbenzenesulfonates, alkanesulfonates, olefin sulfonates, alkyl ether sulfonates, glycerol ether sulfonates, .alpha.-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates. If the anionic surfactants contain polyglycol ether chains, these may have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these may have a conventional homolog distribution, but preferably have a narrowed homolog distribution. Examples of cationic surfactants are quaternary ammonium compounds, such as, for example, dimethyldistearylammonium chloride, and ester quats, in particular quaternized fatty acid trialkanolamine ester salts. Examples of amphoteric or zwitterionic surfactants are alkylbetaines, alkylamidobetaines, aminopropionates, aminoglycinates, imidazoliniumbetaines and sulfobetaines. Examples of particularly suitable mild, i.e. particularly skin-compatible surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, .alpha.-olefinsulfonates, ether carboxylic acids, alkyl oligoglucosides, fatty acid glucamides, alkylamidobetaines, amphoacetals and/or protein fatty acid condensates.

Examples of thickeners that may be included in the formulations and/or compositions of the present invention include, but are not limited to, fatty alcohols or hydroxy fatty alcohols having 12 to 22, and preferably 16 to 18, carbon atoms, and also partial glycerides, fatty acids or hydroxy fatty acids, alkyl oligoglucosides and/or fatty acid N-methylglucamides of identical chain length and/or polyglycerol poly-12-hydroxystearates, aerosil grades (hydrophilic silicas), polysaccharides, in particular xanthan gum, guar guar, agar agar, alginates and tyloses, carboxymethylcellulose and hydroxyethylcellulose, relatively high molecular weight polyethylene glycol mono- and diesters of fatty acids, polyacrylates, polyacrylamides, polymers, polyvinyl alcohol and polyvinylpyrrolidone, ethoxylated fatty acid glycerides, esters of fatty acids with polyols, pentaerythritol or trimethylolpropane, fatty alcohol ethoxylates, alkyl oligoglucosides, and electrolytes such as sodium chloride and ammonium chloride.

Examples of UV-absorbers that may be included in the formulations an/or compositions of the present invention include, but are not limited to, allantoin paba, benzalphthalide, benzophenone, benzophenone-1, benzophenone-10, benzophenone-11, benzophenone-12, benzophenone-2, benzophenone-3, benzophenone-4, benzophenone-5, benzophenone-6, benzophenone-7, benzophenone-8, benzophenone-9, benzyl salicylate, benzylidene camphor sulfonic acid, bornelone, bumetrizole, butyl methoxy-dibenzoylmethane, camphor benzalkonium methosulfate, cinoxate, deamethoxycinnamate, diisopropyl methyl cinnamate, dimethyl paba ethyl cetearyldimonium tosylate, drometrizole, ethyl cinnamate, ethyl dihydroxypropyl paba, ethyl diisopropylcinnamate, ethyl methoxycinnamate, ethyl urocanate, etocrylene, glyceryl octanoate dimethoxycinnamate, glyceryl paba, glycol salicylate, homosalate, isoamyl p-methoxycinnamate, isopropyl dibenzoylmethane, isopropyl methoxycinnamate, isopropylbenzyl salicylate, menthyl anthranilate, menthyl salicylate, n-ethyl-3-nitro paba, octocrylene, octrizole, octyl dimethyl paba, octyl methoxycinnamate, octyl salicylate, octyl triazone, paba, peg-25 paba, phenylbenzimidazole sulfonic acid, polyacrylamidomethyl benzylidene camphor, potassium methoxycinnamate, potassium phenyl-benzimidazole sulfonate, tea-phenyl-benzimidazole sulfonate, tea-salicylate, terephthalylidene dicamphor sulfonic acid, urocanic acid, 3-benzylidene camphor and 4-methylbenzylidene camphor.

UV-A and/or UV-B absorbers may be incorporated into the formulations and/or compositions as defined herein in a range from about 0.1% to about 30% by weight, preferably from about 0.5% to about 10% by weight, in particular from about 1.0% to about 6.0% by weight based on the total weight of the formulations and/or composition in order to provide formulations and/or compositions that protect the skin from the entire range of ultraviolet radiation In one embodiment, the formulations and/or compositions of the invention are formulated and/or prepared for topical administration. The term "topical", as used herein, unless otherwise specified, includes any route of administration that enables the compounds to line the skin or mucosal tissues. The formulations and/or compositions suitable for topical application may be in the form of, for example, a cream, a lotion, a cosmetic serum, a solution, a gel, an ointment, a paste, a bioadhesive, a power or the like. They may also be prepared so as to comprise liposomes, micelles, microparticles and/or microspheres according to known methods and techniques in the art.

In some implementations of this embodiment, the formulations and/or compositions are aqueous (i.e., comprise water) or are substantially non-aqueous (i.e., comprise trace amount of water) or are non-aqueous (i.e., do not comprise water). They may also optionally be used in combination with an occlusive over layer so that moisture evaporating from the body surface is maintained within the formulation and/or composition upon application to the body surface and thereafter.

According to one implementation, the formulations and/or compositions are prepared as creams. Creams, as well known in the art, are viscous liquids or semi-solid emulsions that are divided into two types: oil-in-water (O/W) creams which are composed of small droplets of oil dispersed in a continuous phase, and water-in-oil (W/O) creams which are composed of small droplets of water dispersed in a continuous oily phase. Oil-in-water creams are less greasy and more easily washed off using water. Water-in-oil creams are typically more moisturizing as they provide an oily barrier which reduces water loss from the stratum corneum, the outermost layer of the skin.

The creams of the present invention comprise at least one skin cell activator selected from the group of epidermis activator and dermis activator. For example, the creams comprise at least one epidermal stem cells activator and one dermal stem cells activator.

According to another implementation, the formulations and/or compositions are prepared as a cosmetic serum. Cosmetic serum is a highly concentrated product based on water oil. Serums may comprise about 2 to 5 times or even more of the skin stem cells activator agents (either of the epidermal stem cells activator or of the dermal stem cells activator or of both) than the creams of the invention. Cosmetic serums may work differently upon different parts of the body: face, neck, decollate, eyelids, contour of the eyes and others. Moreover, the pH level of serums used for eyelids should typically be distinct from the pH level of serums used for other parts of the body (the pH level for eyelids is 7 in contrast to the pH level of other serums which varies from 5 to 6.5).

Cosmetic serum of the invention comprises at least one skin cell activator selected from the group of epidermis activator and dermis activator. For example, the cosmetic serum comprises at least one epidermal stem cells activator and one dermal stem cells activator.

The cosmetic serum and creams of the invention may be used in combination. For example, the serum of the invention may be applied to the skin prior to application of the cream of the invention. In this example, the cream creates a protective layer which will conserve the serum against evaporation and the skin against dryness. Cream and serum strengthen each other's action.

According to another implementation, the formulations and/or compositions are prepared as lotion. Lotions are preparations to be applied to the skin surface without friction, and are typically liquid or semi liquid preparations in which solid particles, including the active agent, are present in a water or alcohol base. Lotions are usually suspensions of solids.

According to another implementation, the formulations and/or compositions are prepared as pastes. Pastes are semisolid dosage forms in which the active agent is suspended in a suitable base. Depending on the nature of the base, pastes are divided between fatty pastes or those made from a single-phase aqueous gel.

According to another implementation, the formulations and/or compositions are prepared as ointments. Ointments are semisolid preparations that are typically based on petrolatum or other petroleum derivatives. The specific ointment base to be used, as will be appreciated by those skilled in the art, is one that will provide for optimum treatment of the skin, for improving appearance of the skin.

According to another implementation, the formulations and/or compositions are prepared as gels. As will be appreciated by those working in the field of formulation, gels are semisolid, suspension-type systems. Single-phase gels contain organic macromolecules distributed substantially uniformly throughout the carrier liquid, which is typically aqueous, but also, preferably, contain an alcohol and, optionally, oil.

Examples of skin areas that can be treated and/or that may be applied with the formulations and/or compositions of the invention include but are not limited to, the skin of the face (e.g., forehead, cheeks, eyelids, contour of the eyes, jaw line, chin, nose, hears, etc.), the skin of the neck, the skin of upper torso, the skin of the arms, skin of the legs, skin of the feet, skin of the hands, skin of the elbows, skin of the knees, etc.

As used herein, the term "treated" designates an area of the skin of a subject onto which the formulations and/or the compositions as defined herein have been applied. Before being "treated" these areas of the skin are generally in need of skin care and/or in need of appearance improvement, an increase in firmness, an increase in elasticity, an increase in hydration, a decrease in wrinkle depth, and/or wherein the epidermis is in need of activation, rejuvenation, vitalization, growth, repair, and/or regeneration.

In another embodiment, the present invention provides methods for skin care.

In particular, the present invention provides methods that have the potential of improving appearance of the skin, skin firmness, skin elasticity, skin moisture; the potential of reducing wrinkle depth, of promoting growth, repair, vitalization, regeneration and/or survival of the epidermis and/or epidermal stem cells and potentially the dermis and/or the dermal stem cells.

The methods generally comprise applying an effective amount of the formulations and/or compositions defined herein onto the skin of a subject.

The expression "effective amount", as used herein, unless otherwise specified, refers to an amount effective and for periods of time necessary, to achieve the desired cosmetic result. An effective amount of the skin stem cells activator agent noted herein may vary according to factors such as, the desired cosmetic effect, the desired appearance of the skin, age and sex of the subject, skin health, skin damage, dryness of the skin, overall health of the subject, etc. The number of applications of the formulations and/or compositions on the skin per day may be adjusted to provide the optimum response. An effective amount is also one in which any detrimental effects are outweighed by the beneficial effects.

According to one implementation of this embodiment, the method comprises applying the serum comprising the epidermal stem cells activator and the dermal stem cells activator as defined herein to an area of the skin to be treated. The serum defined herein may be applied to the area of the skin to be treated at least once daily, most particularly, at least twice daily.

According to another implementation of this embodiment, the method comprises applying the cream comprising the epidermal stem cells activator and the dermal stem cells activator as defined herein. The cream defined herein may be applied to the area of the skin to be treated at least once daily, most particularly, at least twice daily.

According to another example, the method comprises applying the serum defined herein to an area of the skin to be treated prior to applying the cream as defined herein to that same area of the skin. The serum and the cream may be applied to the area of the skin to be treated at least once daily, most particularly, at least twice daily. The serum and the cream may be applied more than twice daily for example, in situations where the skin is damaged and is in need of intensive treatment.

It will be understood that other formulations and/or compositions (such as for examples, lotions, gels, ointments, etc.) may be used in the methods defined herein, for example, in combination with the serum and/or the creams defined herein, without departing from the present methods.

In another embodiment, the present invention provides a kit and comprising the formulations and/or compositions as defined herein, together with instructions for application of the formulations and/or compositions to achieve the skin conditions described above.

In one implementation of this embodiment, the kit comprises a serum comprising one or more skin cells activator agents. In particular, the serum includes an epidermal stem cell activator and a dermal stem cell activator and instructions for utilization and/or application of the serum. The serum may, for example, be placed into a suitable container.

In another implementation, the kit comprises a cream comprising one or more skin cells activator agents. In particular, the cream includes an epidermal stem cell activator and a dermal stem cell activator and instructions for utilization and/or application of the cream. The cream may, for example, be placed into a suitable container.

The present invention also provides a kit assembly that comprises both the serum of the invention and the cream of the invention together with instructions for the sequential application of the serum and the cream to achieve the skin conditions as described above.

Suitable containers include, but are not limited to, bottles, tubes, bags, bottles having pump mechanisms (dispenser mechanisms) or squirt bottle tube configurations for dispensing the formulations and/or compositions. Suitable containers also include airless dispensers to maintain the properties of the formulations and/or compositions of the invention. The methods and techniques for packaging the formulations and/or compositions into airless dispensers are known in the art.

The bottles or jars may also have a mouth large enough for an applicator to be dipped into the formulation and/or compositions in the bottles or the jars. The formulations and/or compositions may also be scooped out of the bottles or the jars by hand or fingers and applied to the skin area to be treated.

EXAMPLES

Example 1

Skin Density and Wrinkle Depth and Activation of Epidermis and Dermis

Figure 1:
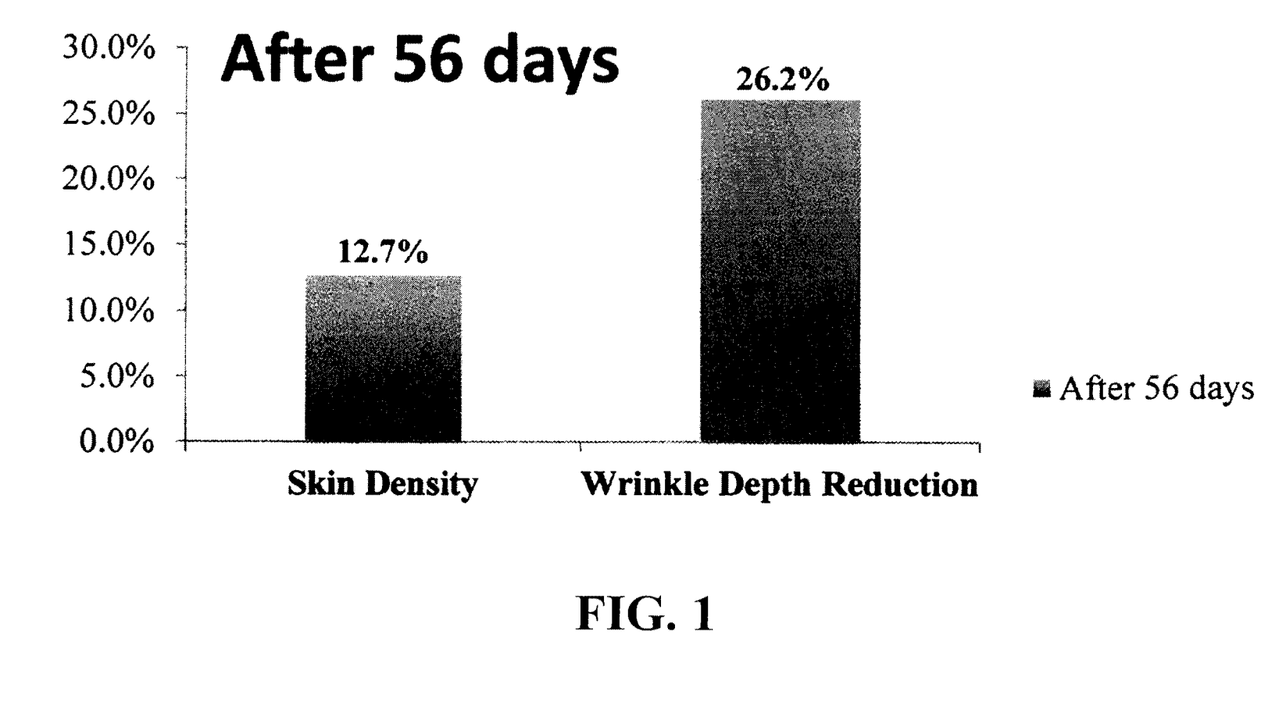
FIG. 1 illustrates a graph showing the effects of a 56 day treatment with *argania spinosa* sprout cell extract on skin density and on wrinkle depth reduction.

An *argania spinosa* sprout cell extract was applied to the skin of nine (9) subjects for a period of 8 weeks (56 days). Skin density and wrinkle depth reduction were assessed throughout the 8 week period. An increased in skin density of 12.7% and a reduction in wrinkle depth of 26.2% were observed after the 8 week treatment period (FIG. 1).

Figure 2:
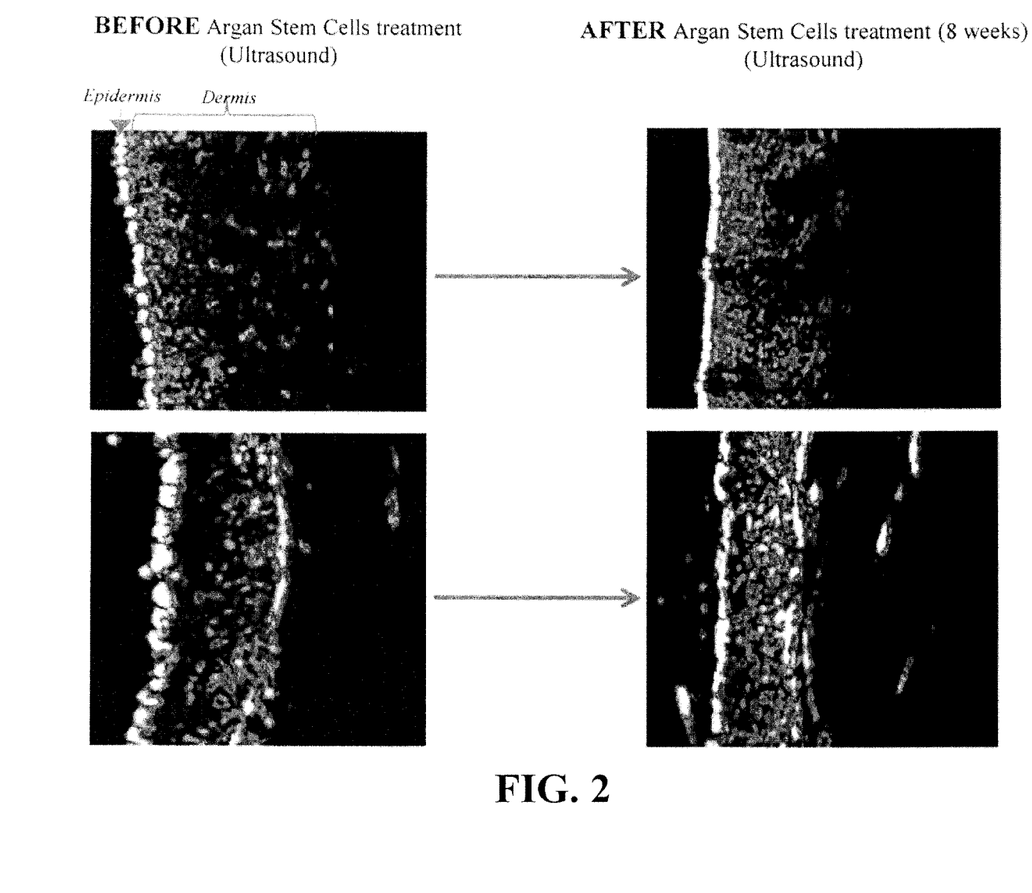
FIG. 2 illustrates a transverse view of the epidermis and dermis before and after a 56 day treatment with *argania spinosa* sprout cell extract.

The epidermis and the dermis of the skin of the subjects before and after treatment with the *argania spinosa* sprout cell extract were observed using ultrasound imaging. Activation (increase in density) of the epidermis and the dermis was observed after 56 days of application of the *argania spinosa* sprout cell extract (FIG. 2).

Example 2

Cream Composition

TABLE 1

| Components (INCI names) | w/w % of total cream composition |
|---|---|
| Water | 54.594908 |
| C12-20 acid PEG-8 ester | 8.000000 |
| Caprylic/capric triglyceride | 6.202500 |
| Squalane | 5.560000 |
| Niacinamide | 5.000000 |
| Butylene glycol | 4.500000 |
| Coco-caprylate/caprate | 3.500000 |
| Glycerin | 3.110500 |
| Myristyl myristate | 3.000000 |
| *Butyrospermum Parkii* (shea butter) | 1.000000 |
| Hydroxyethyl acrylate/sodium acryloyldimethyl taurate copolymer | 0.800000 |
| Phenoxyethanol | 0.757500 |
| Dimethicone | 0.500000 |
| Potassium cetyl phosphate | 0.500000 |
| *Melissa officinalis* leaf extract | 0.400000 |
| Panthenol | 0.300000 |
| Carbomer | 0.300000 |
| Ethylhexylglycerin | 0.300000 |
| Pyridoxine HCl | 0.200000 |
| *Malus domestica* fruit cell culture extract | 0.180000 |
| Parfum (fragrance) | 0.170000 |
| Polysorbate 60 | 0.160000 |
| Disodium EDTA | 0.120000 |
| Sodium hyaluronate | 0.100000 |
| *Aloe barbadensis* leaf juice | 0.100000 |
| *Argania spinosa* sprout cell extract | 0.097250 |
| Lecithin | 0.087960 |
| Sodium hydroxide | 0.084000 |
| *Borago officinalis* seed oil | 0.080000 |
| Tocopheryl acetate | 0.080000 |
| Carnosine | 0.060000 |
| *Brassica campestris* (rapedeed) seed oil | 0.048000 |
| Tetradecyl aminobutyroylvalylaminobutyric urea trifluoroacetate | 0.025000 |
| Xanthan gum | 0.020000 |
| Retinyl palmitate | 0.020000 |
| *Rosmarinus officinalis* (rosemary) leaf extract | 0.012000 |
| *Psilanthus bengalensis* leaf cell culture extract | 0.010000 |
| Cyclodextrin | 0.005250 |
| Ascorbyl tetraisopalmitate | 0.005000 |
| Tocotrienols | 0.002888 |
| *Elaeis guineensis* (palm) oil | 0.002663 |
| Magnesium chloride | 0.002500 |
| Tocopherol | 0.000938 |
| Squalene | 0.000750 |
| Phytosterols | 0.000263 |
| Alcohol | 0.000130 |

Example 3

Serum Composition

TABLE 2

| Components (INCI names) | w/w % of total serum composition |
|---|---|
| Water | 84.214620 |
| Niacinamide | 5.000000 |
| Propanediol | 4.000000 |
| Glycerin | 2.709500 |
| Phenoxyethanol | 0.659000 |
| Sodium hyaluronate | 0.500000 |
| *Melissa officinalis* leaf extract | 0.400000 |
| Panthenol | 0.300000 |
| Ethylexylglycerin | 0.300000 |

TABLE 2-continued

| Components (INCI names) | w/w % of total serum composition |
|---|---|
| Chlorphenesin | 0.270000 |
| Pyridoxine HCL | 0.200000 |
| Acrylates/C10-30 alkyl acrylate crosspolymer | 0.200000 |
| *Argania spinosa* sprout cell extract | 0.194500 |
| *Malus domestica* fruit cell culture extract | 0.180000 |
| PPG-26-buteth-26 | 0.159000 |
| PEG-40 hydrogenated castor oil | 0.114000 |
| Lecithin | 0.088120 |
| *Borago officinalis* seed oil | 0.080000 |
| Tocopheryl acetate | 0.080000 |
| Parfum (fragrance) | 0.080000 |
| Sodium hydroxide | 0.072000 |
| Carnosine | 0.060000 |
| Caprylic/capric triglyceride | 0.060000 |
| Tetradecyl aminobutyroylvalylaminobutyric urea trifluoroacetate | 0.025000 |
| Xanthan gum | 0.020000 |
| Retinyl palmitate | 0.020000 |
| Cyclodextrin | 0.005500 |
| Ascorbyl tetraisopalmitate | 0.005000 |
| Magnesium chloride | 0.002500 |
| *Aloe barbadensis* leaf extract | 0.001000 |
| Alcohol | 0.000260 |

*Malus domestica* Fruit Cell Culture Extract
Potential Effects:
  Protects longevity of epidermal stem cells;
  Delays senescence of epidermal stem cells;
  Increases the vitality of skin epidermal stem cells; and
  Combats chronological ageing.
*Argania Spinosa* Sprout Cell Extract and Isomalt and Lecithin
Potential Effects:
  Helps protect and vitalize human dermal stem cells;
  Enhances the maintaining of pluripotency of human dermal stem cells;
  Accelerates skin's natural repair process;
  Restores the skin's firmness and reduce wrinkles; and
  Reactivates all of the skin's youthful functions.
  A combination of epidermal with dermal stem cell activators has the potential to enhance youthfulness of the skin resulting in superior (compared to the use of either epidermal or dermal stem cells activators individually) firming, skin thickness, collagen production and overall quality of skin anti-ageing characteristics.
Tripeptide: Tetradecyl Aminobutyroylvalylaminobutyric Urea Trifluoroacetate
Potential Effects:
  Stimulates production of hyaluronic acid and enhancing collagen fibrils.
Multi Vitamin Cocktail
Potential Effects:
  Powerful anti-oxidants;
  Anti-inflammatory;
  Improves hydration of the skin as well as skin texture;
  Enhances cellular regeneration; and
  Improves skin recovery after UV exposure as well as having a preventative effect against UV damage.
Sodium Hyaluronate:
Potential Effects:
  Enhances hydration, texture and elasticity.
Aloe Barbadensis Leaf Juice:
Potential Effects:
  Hydration, enhanced texture.
*Melissa officinalis* Leaf Extract and Lecithin and Carnosine and Cyclodextran:
Potential Effects:
  Anti-glycation of structural proteins;
  Anti-inflammatory;
  Decreases collagen degradation; and
  Enhanced hydration, firmness and elasticity.

Example 4

Hydration of the Skin

The cream composition and the serum composition defined in Examples 2 and 3 were applied to facial skin of nine (9) human subjects twice daily for 8 weeks (56 days).

For each application, an amount of between about 0.01 ml and about 1 ml of the serum composition was applied to a facial skin area. The serum was allowed to penetrate into the skin for about 20 seconds. An amount of between about 0.01 ml and about 1 ml of the cream composition was then applied to the same skin area. Moisture of the skin in the treated area was measured throughout the 8 week period using a Multi Dermascope MDS800® (which measured moisture on a scale of 0 to 99) (Courage and Khazaka, Cologne, Germany). The measurements demonstrated an increase in skin moisture of about 200% (see Table 3 below for examples of data obtained).

TABLE 3

Samples of moisture measurements

| Patient | Hydration at day 1 (unit/scale 0-99) | Hydration at day 56 (unit/scale 0-99) |
|---|---|---|
| 1 | 33 | 94 |
| 2 | 27 | 81 |
| 3 | 29 | 87 |

Example 5

Elasticity of the Skin

The cream composition and the serum composition defined in Examples 2 and 3 were applied to facial skin of nine (9) human subjects twice daily for 8 weeks.

For the application, an amount of between about 0.01 ml and about 1 ml of the serum composition was applied to a facial skin area. The serum was allowed to penetrate into the skin for about 20 seconds. Then, an amount of between about 0.01 ml and about 1 ml of the cream composition was applied to the same facial area. Elasticity of the skin in the treated area was measured throughout the 8 week period using a Multi Dermascope MDS800® (which measured moisture on a scale of 0 to 99) (Courage and Khazaka, Cologne, Germany). The measurements demonstrated an increase in skin elasticity of about 20% (see Table 4 below for examples of data obtained).

TABLE 4

Samples of elasticity measurements

| Patient | Elasticity at day 1 (%) | Elasticity at day 56 (%) |
|---|---|---|
| 1 | 59 | 80 |
| 2 | 40 | 52 |
| 3 | 57 | 69 |

Example 6

Subjects' Auto-Evaluations

The effects of the serum and cream compositions of Examples 2 and 3 were also evaluated through subjects' auto-evaluations. Results of the subjects' auto-evaluations are presented in Table 5 below:

TABLE 5

| Effects | Comments |
|---|---|
| Rejuvenation and revitalization | My skin feels rejuvenated<br>My skin looks revitalized |
| Youth | My skin looks visibly younger<br>My skin looks visibly more youthful<br>Fine wrinkles have decreased<br>Fine wrinkle have disappeared<br>My skin looks visibly smoother<br>My skin looks lifted<br>My skin feels lifted |
| Radiance and glow | My skin's imperfections are attenuated<br>My skin looks/is more radiant<br>My skin looks more glowing |
| Firmness and elasticity | My skin looks firmer<br>My skin looks tighter<br>My skin feels tighter |
| Hydration | My skin is more hydrated<br>My skin is intensely hydrated |
| Tonicity | The tonicity of my skin improved |
| Healthiness | My skin looks healthier<br>My skin feels healthier<br>My skin looks smooth<br>My skin feels silky |
| Performance and recommendation | I would recommend this product<br>I believe the performance of this product is superior to my current cream/serum<br>I believe that the serum and the cream have the best performance to all creams and serums<br>I will switch to this product from my current cream/serum |

It is understood that the data reported in the present specification are only given to illustrate the invention and may not be regarded as constituting a limitation thereof.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All published documents mentioned in the present specification are herein incorporated by reference.

BIBLIOGRAPHY

1. Biernaskie J. et al. 2009. SKPs derive from hair follicle precursors and exhibit properties of adult dermal stem cells. Cell Stem Cell. December 4; 5(6):610-23.
2. Schmid D. et al. 2008. Plant Stem Cell Extract for Longevity of Skin and Hair. SOFW Journal (English Edition) 134; 5-2008:29-35.

What is claimed is:

1. A cosmetic composition for improving overall skin appearance through activation of skin stem cells, comprising:
   a) between about 0.01% and about 10% by weight of the composition of malus domestica extract;
   b) between about 0.01% and about 5% by weight of the composition of argania spinosa sprout extract; and
   c) a mixture comprising effective amounts of: hyaluronic acid, melissa officinalis leaf extract, and aloe barbadensis leaf extract;
   wherein the argania spinosa sprout extract is encapsulated; and
   wherein the cosmetic composition is selected from: a serum, a cream, a lotion, and an ointment.

2. The cosmetic composition as defined in claim 1, wherein the encapsulation is a double encapsulation.

3. The cosmetic composition as defined in claim 1, further comprising a tripeptide, vitamins, and aloe juice.

4. The cosmetic composition as defined in claim 1, further comprising isomalt, lecithin, carnosine and cyclodextran.

5. The cosmetic composition as defined in claim 1, wherein the melissa officinalis leaf extract is present in an amount of about 0.4% by weight of the cosmetic composition.

6. The cosmetic composition as defined in claim 1, wherein aloe barbadensis leaf extract is present in an amount of at least about 0.001% by weight of the cosmetic composition.

7. A method for improving overall skin appearance through activation of skin stem cells of a subject in need thereof, comprising applying the cosmetic composition as defined in claim 1 to the skin of said subject.

8. The method as defined in claim 7, wherein the skin stem cells are epidermal stem cells and dermal stem cells.

9. A method for delaying onset of skin ageing through activation of skin stem cells of a subject in need thereof, comprising applying the cosmetic composition as defined in claim 1 to the skin of said subject.

* * * * *